(12) United States Patent
Bogaert

(10) Patent No.: US 8,871,828 B2
(45) Date of Patent: Oct. 28, 2014

(54) ADHESIVE CREAM

(76) Inventor: Jean Pierre Bogaert, Monte Carlo (MC)

( * ) Notice: Subject to any disclaimer, the term of this patent is extended or adjusted under 35 U.S.C. 154(b) by 2 days.

(21) Appl. No.: 13/574,224

(22) PCT Filed: Jan. 19, 2011

(86) PCT No.: PCT/EP2011/000195
§ 371 (c)(1),
(2), (4) Date: Aug. 17, 2012

(87) PCT Pub. No.: WO2011/088988
PCT Pub. Date: Jul. 28, 2011

(65) Prior Publication Data
US 2013/0197124 A1    Aug. 1, 2013

(30) Foreign Application Priority Data

Jan. 19, 2010 (CH) .......................... 74/10
May 6, 2010 (CH) .......................... 701/10

(51) Int. Cl.
C08L 35/08  (2006.01)
C08L 1/08   (2006.01)
C08L 71/02  (2006.01)
A61K 6/00   (2006.01)

(52) U.S. Cl.
CPC ............ *A61K 6/0023* (2013.01); *A61K 6/0026* (2013.01)
USPC ........................................................ 523/105

(58) Field of Classification Search
None
See application file for complete search history.

(56) References Cited

U.S. PATENT DOCUMENTS

| 3,003,988 | A | * | 10/1961 | Germann et al. ............. 524/474 |
| 4,569,955 | A | * | 2/1986 | Dhabhar ....................... 523/120 |
| 4,758,630 | A | | 7/1988 | Shah et al. |
| 5,051,130 | A | * | 9/1991 | Futami et al. ................... 106/35 |
| 5,561,177 | A | * | 10/1996 | Khaledi et al. .................. 524/35 |
| 6,592,851 | B2 | * | 7/2003 | Warford et al. ................. 424/49 |
| 2004/0141933 | A1 | * | 7/2004 | Luo et al. ........................ 424/64 |

* cited by examiner

*Primary Examiner* — James J Seidleck
*Assistant Examiner* — Peter A Salamon
(74) *Attorney, Agent, or Firm* — Morriss O'Bryant Compagni, PC

(57) ABSTRACT

Improved composition of a fixing cream, in particular for tooth prostheses, containing at least one oil and/or fat, preferably of a plant type, at least one water-soluble polymer selected from the group of cellulose derivatives, at least one alkyl vinyl ether/maleic acid anhydride copolymer,
the fatty acid content of the plant oil or fat contained consisting of at least 20% by weight of unsaturated fatty acids.

44 Claims, No Drawings

ADHESIVE CREAM

CROSS-REFERENCE TO RELATED APPLICATIONS

This application is a national phase entry under 35 U.S.C. §371 of PCT/EP2011/000195 filed Jan. 19, 2011, which claims priority to Swiss Patent Application No. 00074/10 filed Jan. 19, 2010 and Swiss Patent Application No. 00701/10 filed May 6, 2010, the entirety of each of which is incorporated his reference.

BACKGROUND

1. Field of the Invention

The invention relates to an adhesive cream composition.

2. Prior Art

Many commercial adhesive cream compositions for prosthetic teeth are based on a mixture of refined paraffins, water-soluble cellulose derivative polymers and alkyl vinyl ether/maleic acid anhydride copolymers. Conventionally, mineral oils and mineral fats, in particular Vaseline, are used. Mineral oils and mineral fats generally constitute approximately 40% by weight or more of the adhesive cream composition.

Since an adhesive cream slowly dissolves in the mouth during use, on the one hand there is the possibility that components of the adhesive cream enter the body via the mucous membranes of the mouth and pharynx and, on the other hand, components reach the digestive tract with the saliva and the food and may subsequently become distributed throughout the body. The basic components of Vaseline and mineral oil are not completely harmless according to the most recent results of research. Vaseline, for example, appears to promote blastomycosis conditions in newborn babies. Consequently, negative effects in adults cannot be excluded. Caution appears to be demanded particularly in the regular use of mineral oils on mucous membranes. Therefore, a replacement for mineral oils and mineral fats would be desirable.

In order to improve adhesion, zinc-containing substances are generally added. Such commercial adhesive cream products have a zinc content of from 1.7 to 3.4% by weight according to in-house analyses. In document U.S. Pat. No. 4,758,630, a zinc content of from 1 to 2.4% by weight of the total amount of adhesive cream composition is recommended. Recently, it has also become known that greater absorption of zinc compounds by the organism which had previously been thought to be harmless sometimes causes irreversible symptoms of poisoning. With regular use, therefore, the zinc compounds in the adhesive cream could have similar effects. In order to prevent toxic symptoms in tooth prosthesis wearers, there is a need for an adhesive cream formulation which also has excellent wearing properties and storability with addition of zinc compounds which is reduced or dispensed with.

Furthermore, commercial base products which are used in the production of adhesive creams in any case contain traces of zinc impurities such as, for example, Gantrez® MS955, a methyl vinyl ether/maleic acid anhydride copolymer which is often used in the production of adhesive creams. Analyses have shown that this base product contains 4.8 mg of zinc per kilogram. As a result, a content of approximately 2 ppm of zinc, but a maximum of 4.8 ppm of zinc, may be anticipated in an adhesive cream produced therewith. However, the proportion of zinc compounds which may be contained in such base products is far lower than that which is measured—as mentioned above—in commercial adhesive creams and originates from selective addition.

If currently existing formulations with a methyl vinyl ether/maleic acid anhydride copolymer could be modified in such a manner that it is possible to dispense, partially, or completely, with mineral oils and/or Vaseline and additionally included zinc compounds, there would result a product which can be regarded as being harmless to health. In particular the use of plant oils and fats would correspond to the current health consciousness of consumers.

The contents and the quantitative relationships determine the properties of an adhesive cream. The properties include, for example, the adhesion strength, the adhesion duration, the wearing comfort, the taste, the consistency, the stability, etcetera. In order to adjust the adhesion parameters such as adhesion duration and adhesion strength, a given proportion of $Zn^{2+}$ compounds is added in commercial products on a mineral oil basis. The adhesion strength and the adhesion duration are positively influenced by the addition of zinc compounds according to document U.S. Pat. No. 4,758,630 and, consequently, the addition of zinc compounds is of great significance to the usability of the adhesive cream.

As mentioned above, paraffins such as refined mineral oils and fats (Vaseline) are used in many commercial adhesive creams. These are admixtures of saturated hydrocarbons having the general molecular formula $C_nH_{2n+2}$, this involving liquid products (oils) or greasy to solid products (fats) in accordance with the distillation degree. The mineral oil admixtures and fats which are used in cosmetics and medicine also consist of practically exclusively saturated hydrocarbons. The purity of the admixtures depends on the degree of refinement. The degree of refinement is high for cosmetic and medical use. It is thereby intended to be ensured that carcinogenically acting polycyclical aromatic hydrocarbons are removed from the admixture as completely as possible.

Mineral oils and fats are often used as bases of skin adhesive creams, the effect thereof being graded differently in this instance. Acknowledged groups of experts are of the opinion that paraffins can prevent the natural regulation mechanisms of the human body. In particular, they can accumulate in the liver, kidney and lymph nodes. However, there is uncertainty as to whether the paraffins can penetrate the skin. It is generally assumed that paraffins do not penetrate the skin in the case of topical application and therefore there is also no risk from those substances. Cosmetic skin adhesive creams having oils and fats have been on the market for many years. In the case of use in adhesive creams, however, there is an increased probability that paraffinic components will be absorbed directly by the body via the digestion. Document U.S. Pat. No. 5,561,177 discloses an adhesive cream formulation which is produced on the basis of plant oils. Accordingly, oils which particularly contain triglycerides of saturated fatty acids can be successfully used. Those triglycerides further have carbon chains of medium length, that is to say, chains having 8 or 10 carbon atoms in the fatty acid radical, which do not correspond to the typical fatty acid range of plant oils and fats ($C_{12}$-$C_{20}$). The use of oils which contain unsaturated fatty acids is not recommended. According to U.S. Pat. No. 5,561,177, oils which contain unsaturated fatty acid esters have the disadvantage that they become unstable at high temperatures or after being stored for a given time. Furthermore, adhesive creams which contain such oils are less solid owing to the unsaturated double-bonds present, that is to say, too liquid to be used as an adhesive cream.

SUMMARY OF THE INVENTION

The present invention provides an adhesive cream composition which has good adhesive strength and is stable in the long term. Furthermore, the adhesive cream composition is intended to be based on predominantly natural and physiologically harmless base products. In particular, there is intended to be found a formulation which is also free from mineral oils and free from zinc-containing compounds or which may have good adhesive cream properties with a low content of mineral oil and/or zinc. The adhesive cream is improved in physiological terms and is at least equivalent in terms of its stability properties and adhesion properties, in particular with regard to the adhesion duration and the adhesion strength, in comparison with commercial adhesive creams. Furthermore, an adhesive cream which produces a pleasant sensation in the mouth is provided.

DETAILED DESCRIPTION OF THE INVENTION

According to the invention, an adhesive cream, in particular for tooth prostheses, contains a) at least one oil and/or fat, that may be of a plant type, b) at least one water-soluble polymer selected from the group of cellulose derivatives and c) at least one alkyl vinyl ether/maleic acid anhydride copolymer, wherein the fatty acid content of the plant oil or fat contained consists of at least 20% by weight of unsaturated fatty acids.

The term fatty acid is used in this instance and below, where applicable, with the meaning of a fatty acid radical. A plant oil or fat is a triester of higher fatty acids with glycerol, that is to say, a fatty acid glycerol ester having three long-chained fatty acids which are also referred to as fatty acid radicals. The fatty acid content is intended to refer below to the fatty acid bound as an ester.

The composition according to the invention has the advantage that it comprises physiologically completely harmless components and is therefore also harmless when used for a relatively long time. Surprisingly, it was possible to find a composition which ensures very good and long-lasting adhesion in spite of a high proportion of unsaturated fatty acids. Good storage stability was also able to be achieved.

In this construction of the invention which is characterised in that the plant oil or fat contains a given minimum unsaturated fatty acid proportion, particularly advantageous adhesion properties are obtained if the composition of the adhesive cream contains additional substances selected from the group consisting of silicon dioxide, talcum, stearates, magnesium stearate, aluminium stearate, phosphoglycerides, polyethylene glycols (also polyoxymethylenes) and trihydroxystearin.

It has surprisingly been found that the flowability and the consistency of the adhesive cream can be positively influenced by the addition of silicon dioxide. A tendency towards liquefaction can effectively be prevented by silicon dioxide.

It has also surprisingly been found that the adhesion properties of the adhesive cream are improved by the addition of trihydroxystearin.

It has surprisingly been established that the high proportion of zinc compounds normally added in order to adjust the adhesion parameters can be dispensed with if one or a plurality of plant oils and/or fats are used simultaneously. Plant oils and fats are obtained from the seeds or fruits of oily plants. In chemical terms, plant oils and fats are esters of glycerin with fatty acids, often with three fatty acids, so-called triglycerides. Many plant oils are regularly taken up by humans with foodstuffs and are physiologically completely harmless in the quantities which generally occur in the food. Examples of the oils and fats which can be used in the adhesive cream composition according to the invention are olive oil, rapeseed oil, peanut oil, maize oil, wheat-germ oil, walnut oil, grapeseed oil, sunflower oil, wheat-germ oil, sesame oil, palm oil, palm seed oil, poppy oil, linseed oil, pumpkin seed oil, thistle oil, evening primrose oil, hemp oil and coconut fat. In this instance, olive oil is used because it results in a particularly physiologically tolerable adhesive cream which is accepted in terms of taste, with the addition of zinc compounds simultaneously being dispensed with. As known, refined olive oil has a relatively neutral taste, is readily available and is generally known to be healthy and digestible. A particular advantage of olive oil is also that it has an antiseptic and antibacterial effect. Tests have shown that, surprisingly, olive oil substantially inhibits the growth of organisms (bacteria, fungi) between the gums and the prosthesis. In particular, it was also possible to establish that the fungus *Candida albicans* can be inhibited by means of the adhesive cream enriched with olive oil.

Particularly surprising results are achieved with the combination of plant oils in adhesive creams with silicon dioxide additives. Plant oils and fats are liquid, or at least highly flowable, owing to their high double-bond proportions. In order to prevent the adhesive cream from flowing away under the prosthesis and, at the same time, to influence the adhesion properties, various stabilizers can be introduced into the adhesive cream admixture. Silicon dioxide has been found to be particularly suitable. In particular, not only is a long adhesion duration achieved with constantly good adhesion strength, but also the stability is provided under adverse environmental conditions, such as, for example, during transport of the adhesive cream in aircraft at reduced pressure or during storage in elevated mountain locations. Silicon dioxide ($SiO_2$) is available in various forms and qualities. Silicon dioxide in the form of highly dispersed silicon dioxide is used (that is to say, in the form of an amorphous silicic powder produced by means of flame methods), also known as pyrogenic silicic acid (Aerosil®).

Consequently, the adhesive cream according to the invention is distinguished by a composition which is harmless to health and which is based on plant oils and/or fats, in particular olive oil. In this instance, olive oil may equally be used in the partially refined and the unrefined state. Cold-pressed olive oil and olive oil produced in a protective manner without any excessive temperature effect from a first pressing is advantageously used (that is to say, native extra virgin olive oil). The plant oil used advantageously consists of a majority of olive oil.

In addition to silicon dioxide, trihydroxystearin and polyethylene glycol also result in stable adhesive cream compositions. These substances provide good results both for adhesive creams on the basis of plant oils and for adhesive creams on the basis of mineral oils.

The adhesive cream advantageously contains in relation to the total quantity of the composition a) from 25 to 60% by weight of at least one oil and/or fat, such as of the plant type b) from 10 to 40% by weight, or from 20 to 40% by weight, of at least one water-soluble polymer selected from the group of cellulose derivatives an c) from 25 to 45% by weight of at least one alkyl vinyl ether/maleic acid anhydride copolymer.

This adhesive cream composition advantageously further contains:

d) from 0 to 15% by weight of polyethylene glycols or optionally up to 15% by weight of polyethylene glycols, e) from 0 to 3% by weight of phosphoglycerides or optionally up to 3% by weight of phosphoglycerides, f) from 0 to 2.5% by weight of trihydroxystearin or optionally up to 2.5% by weight of trihydroxystearin, g) from 0 to 5% by weight of silicon dioxide or optionally up to 5% by weight of silicon dioxide, and h) from 0 to 10% by weight of other additives.

The additives are advantageously selected from the group of stabilizers, thickeners, emulsifiers, antioxidants, flavorings, colorings and admixtures thereof. In this instance, a substance may belong to a plurality of effective groups, or have a plurality of effects.

The stabilizers act in an emulsifying, thickening manner and prevent the components from becoming separated. According to the invention, the stabilizers are selected from the group containing silicon dioxide, trihydroxystearin, phosphoglycerides and polyethylene glycols. These substances have complex effect mechanisms and can influence each other—in accordance with our experiences—synergistically. The stability of an adhesive cream significant during storage and keeping and for the duration of use. During storage and keeping, moisture, temperature and pressure are generally relatively constant. In the course of use, however, oral saliva, food and changing pressure and temperature conditions further act on the adhesive cream. Owing to this changing requirement, it may be advantageous to add different stabilizer substances which in total in the case of the different environmental influences improve and particularly stabilize the adhesive cream properties. Thickeners are used as stabilizers. Thickeners which are also referred to as thickening stabilizers are added in a quantity of from 0.001 to 3% by weight in relation to the total quantity of the composition. The use of silicon dioxide is expedient a quantity of from 0.001 to 5% by weight, from 0.1 to 4% by weight or from 0.5 to 3% by weight in relation to the total quantity of the composition. Particular advantages are involved in the use of silicon dioxide in combination in an adhesive cream on the basis of plant oil and/or fat. It is advantageous to use trihydroxystearin and/or phosphoglycerides such as, for example, lecithins. Trihydroxystearin is advantageously used in a quantity of from 0.001 to 2.5% by weight in relation to the total quantity of the composition and has an emulsifying and thickening effect. There is used a quantity with a lower limit of 0.001% by weight and 0.01% by weight of trihydroxystearin and an upper limit of 2.0% by weight, of 1.5% by weight or of 0.5% by weight of trihydroxystearin, the upper limits and lower limits being able to be freely combined. Polyethylene glycols are advantageously added in a quantity of from 0.001 to 15% by weight, from 3 to 12% by weight or from 5 to 9% by weight in relation to the total quantity of the composition. There is used polyethylene glycols having a molar mass of from 100,000 to 7,000,000 g/mol, in particular from 200,000 to 400,000 g/mol. Phosphoglycerides are advantageously used in a quantity of from 0.001 to 3% by weight in relation to the total quantity of the composition and act in an emulsifying and softening manner. There is used a quantity with a lower limit of 0.001% by weight or 0.01% by weight of phosphoglyceride and an upper limit of 2% by weight, of 1% by weight, or of 0.5% by weight of phosphoglyceride, the upper limits and lower limits being able to be freely combined. If phosphoglycerides such as, for example, lecithin and trihydroxystearin, are present together as stabilizers, the total quantity of stabilizer additive can surprisingly be reduced. If phosphoglycerides and trihydroxystearin are present in combination, phosphoglycerides are advantageously used in a quantity of from 0.001 to 3% by weight, in a quantity of from 0.001 to 2% by weight, or in a quantity of from 0.01 to 1% by weight, and trihydroxystearin in a quantity of from 0.001 to 2.5% by weight, in a quantity of from 0.001 to 1% by weight, or in a quantity of from 0.01 to 0.5% by weight in relation to the total quantity of the composition. Phosphoglycerides, in particular lecithin, more particularly soya lecithin, appear to act in a predominantly stabilising manner on the adhesive cream composition. Stearins, in particular trihydroxystearin, further increase the adhesion strength of the adhesive cream.

In addition to the used stabilizers from the group containing silicon dioxide, trihydroxystearin and phosphoglycerides, other stabilizers or filling substances which act in a thickening manner can be used such as, for example, polyethylene glycol or talcum. Silicon dioxide or trihydroxystearin are used as stabilizers which act in a thickening manner.

An expedient aspect is the combination of the two additives phosphoglycerides and trihydroxystearin, in particular lecithin and trihydroxystearin, with at least one other additive or both additives from the group comprising silicon dioxide and polyethylene glycol.

It is particularly preferable to have an adhesive cream composition in which at least the additives phosphoglyceride, silicon dioxide, trihydroxystearin and optionally polyethylene glycol are present in combination. Particularly suitable phosphoglycerides are lecithins.

An adhesive cream composition in which at least the additives lecithin, silicon dioxide, polyethylene glycol and trihydroxystearin are present in combination is very particularly preferable.

The fatty acids of the added plant oil and/or fat, that is to say, the entirety of the fatty acids, generally consist of at least 20% by weight of unsaturated fatty acids. The content of unsaturated fatty acids in the added plant oil and/or fat is at least 40% by weight, 50% by weight, 60% by weight, 70% by weight or at least 80% by weight of unsaturated fatty acids. This involves the advantage that the adhesive cream is particularly tolerable for the prosthesis wearer during swallowing.

The fatty acid content of the plant oil or fat consists of at least 20% by weight, at least 30% by weight, a majority, that is to say, more than 50% by weight, at least 65% by weight or at least 80% by weight, of fatty acids having a chain length of 12 or more C atoms, in particular from 12 to 26 C atoms. The fatty acid content of the plant oil or fat consists of higher fatty acids having a chain length of from 14 to 24 C atoms, from 14 to 22 or from 16 to 18 C atoms.

Oil and/or fat is contained in the adhesive cream in a quantity of at least 25% by weight, more than 30% by weight, or more than 35% by weight in relation to the total quantity of the composition. Advantageously, the plant oil and/or fat is present in a quantity of a maximum of 60% by weight, or a maximum of 42% by weight in relation to the total quantity of the composition. This results in a preferred range of from 25 to 42% by weight in relation to the total quantity of the composition. The quantity of plant oil or fat influences the consistency of the composition. If too little is added, the adhesive cream may take up a consistency which is dry in a granular manner. The addition of silicon dioxide, trihydroxystearin, phosphoglycerides and polyethylene glycols can counteract this.

The plant oil and/or fat may expediently be provided in the unrefined or refined state.

The higher fatty acids mentioned advantageously comprise a proportion of from 50 to 90% by weight of oleic acid and a residual proportion of other fatty acids having a chain length of from 16 to 18 C atoms. The higher fatty acids comprise a proportion of from 50 to 90% by weight of oleic acid, a proportion of from 5 to 25% by weight of palmitic acid and, optionally, a residual proportion of other fatty acids having a chain length of from 16 to 18 C atoms. The higher fatty acids comprise a proportion of from 50 to 90% by weight of oleic acid, a proportion of from 5 to 25% by weight of palmitic acid, a proportion of from 3 to 25% by weight of linoleic acid and, optionally, a residual proportion of other fatty acids having a chain length of from 16 to 18 C atoms. Oils such as olive oil and rapeseed oil are included by the groups mentioned.

The cellulose derivatives are water-soluble polymers, selected from the group consisting of methyl cellulose, carboxymethyl cellulose, sodium carboxymethyl cellulose, hydroxypropyl methyl cellulose and admixtures thereof. Carboxymethyl cellulose, in particular sodium carboxymethyl cellulose, is used. The water-soluble polymer selected from the group of cellulose derivatives is present in a quantity of from 15 to 45% by weight in relation to the total quantity of the composition. The water-soluble polymer selected from the group of cellulose derivatives is present in a quantity of from 10 to 40% by weight, from 20 to 40% by weight or in a quantity of from 25 to 38% by weight in relation to the total quantity of the composition.

The alkyl vinyl ether/maleic acid anhydride copolymer is advantageously present partially as an acid, ester and/or salt. Generally, the cations of the salts are selected from the group consisting of calcium, potassium, sodium, magnesium, aluminium, zinc salts and admixtures thereof, in particular from the group consisting of $Ca^{2+}$, $K^+$, $Na^+$, $M^{2+}$, $Al^{3+}$ and/or $Zn^{2+}$. In particular, a methyl vinyl ether/maleic acid anhydride copolymer is used as the alkyl vinyl ether/maleic acid anhydride copolymer. The alkyl vinyl ether/maleic add anhydride copolymer is present, for example, as a salt, ester and/or add, in a quantity of from 20 to 45% by weight in relation to the total quantity of the composition. Advantageously, the alkyl vinyl ether/maleic acid anhydride copolymer is present, for example, as a salt and/or acid in a quantity of from 25 to 40% by weight, from 25 to 39.5% by weight or from 28 to 39% by weight in relation to the total quantity of the composition.

Zinc compounds are advantageously not present; that is to say, addition of zinc compounds is advantageously dispensed with. In particular in order to minimise health risks owing to elevated absorption of zinc owing to adhesive creams, the zinc content should be limited to an upper limit of a maximum of 1% by weight. That is to say that zinc may be contained in a quantity of up to 1% by weight in relation to the total quantity of the composition. The zinc content should advantageously be below an upper limit of 1% by weight, of 0.5% by weight, of 0.1% by weight or of 0.06% by weight in relation to the total quantity of the composition, respectively.

However, the absence of any zinc or any zinc compounds is most preferred. Zinc compounds having a lower limit of at least 0.001% by weight, at least 0.01% by weight, at least 0.02% by weight, or at least 0.03% by weight in relation to the total quantity of the composition are optionally present, respectively. In this instance, the upper limit and lower limit may be freely combined. In combination with the above-mentioned oil contents, the zinc quantity may be kept low. The lower limits result on the basis of a measurable effect (that is to say, influence of the adhesion properties) or a desired effective strength as a result of the zinc content.

Adhesive creams having very good wearing properties and long-term stability values are particularly achieved when the above-mentioned oil or fat content, in particular of olive oil, is complied with. Alternatively or additionally, the properties can be adjusted by using and optimising the stabilizers described.

Other additives such as, for example, flavorings, antioxidants and colorings, are present in total in a quantity of a maximum of 10% by weight, a maximum of 2% by weight or a maximum of 1% by weight in relation to the total quantity of the composition. With regard to the physiological harmlessness, the addition quantity of additives is kept as low as possible.

Other additives such as, for example, flavorings, antioxidants and colorings, are present in total in a quantity of a maximum of 10% by weight, a maximum of 2% by weight or a maximum of 1% by weight in relation to the total quantity of the composition. With regard to the physiological harmlessness, the addition quantity of additives is kept as low as possible.

The invention is explained below with reference to examples. The examples set out compositions which ensure good adhesion strength and adhesion duration, in particular also under reduced pressure conditions. The percentages are rounded to two places after the decimal point.

Example 1

| Component | % by weight |
|---|---|
| Olive oil[1] | 40.35 |
| Alkyl vinyl ether/maleic acid anhydride copolymer | 30.26 |
| Carboxymethyl cellulose | 27.24 |
| ZnO paste[2] | 0.10 |
| Trihydroxystearin | 2.02 |
| Aromatic additive | 0.03 |

[1] commercially available,
[2] the paste consists of 50% by weight of oil (for example, olive oil) and 50% by weight of zinc oxide (ZnO), consequently approximately 0.04% by weight of zinc is added in the form of the ZnO paste.

The adhesive cream according to example 1 has good adhesion strength which lasts at least 12 hours. The adhesive cream leaves behind a fresh taste and a good, pleasantly silky sensation in the mouth.

Example 2

| Component | % by weight |
|---|---|
| Olive oil[1] | 31.19 |
| Alkyl vinyl ether/maleic acid anhydride copolymer | 32.22 |
| Carboxymethyl cellulose | 36.38 |
| ZnO paste[2] | 0.16 |
| Trihydroxystearin | 0.03 |
| Lecithin | 0.02 |
| Aromatic additive[3] | 0.00 |

[1] commercially available,
[2] the paste consists of 50% by weight of oil (for example, olive oil) and 50% by weight of zinc oxide (ZnO), consequently approximately 0.064% by weight of zinc is added in the form of the ZnO paste,
[3] the added quantity is below measurement accuracy, in particular below 0.01% by weight.

The adhesive cream according to example 2 has good adhesion strength which lasts at least 12 hours. The adhesive cream leaves behind a fresh taste and a good, pleasantly silky sensation in the mouth.

Example 3

| Component | % by weight |
|---|---|
| Olive oil[1] | 36.99 |
| Alkyl vinyl ether/maleic acid anhydride copolymer | 37.51 |
| Carboxymethyl cellulose | 24.91 |
| ZnO paste[2] | 0.09 |
| Trihydroxystearin | 0.45 |

| Component | % by weight |
|---|---|
| Lecithin | 0.05 |
| Aromatic additive[3] | 0.00 |

[1] commercially available,
[2] the paste consists of 50% by weight of oil (for example, olive oil) and 50% by weight of zinc oxide (ZnO), consequently approximately 0.036% by weight of zinc is added in the form of the ZnO paste,
[3] the added quantity is below measurement accuracy, in particular below 0.01% by weight.

The adhesive cream according to example 3 has good adhesion strength which lasts at least 12 hours. The adhesive cream leaves behind a fresh taste and a good, pleasantly silky sensation in the mouth. This adhesive cream further has good long-term stability over months and is consequently storable.

Example 4

| Component | % by weight |
|---|---|
| Olive oil[1] | 38.6 |
| Alkyl vinyl ether/maleic acid anhydride copolymer | 33 |
| Carboxymethyl cellulose | 20 |
| Silicon dioxide | 0.8 |
| Polyethylene glycol | 7 |
| Trihydroxystearin | 0.4 |
| Lecithin[2] | 0.2 |
| Aromatic additive[3] | — |

[1] commercially available,
[2] soya lecithin,
[3] optional.

The adhesive cream according to example 4 has good adhesion strength which lasts at least 12 hours. The adhesive cream leaves behind a fresh taste and a good, pleasantly silky sensation in the mouth. This adhesive cream further also remains stable under reduced pressure conditions, as exist in aircraft freight compartments and residential areas at high elevations.

Example 5

| Component | % by weight |
|---|---|
| Olive oil[1] | 38.58 |
| Alkyl vinyl ether/maleic acid anhydride copolymer | 33.00 |
| Carboxymethyl cellulose | 27.00 |
| Trihydroxystearin | 0.40 |
| Silicon dioxide[2] | 0.80 |
| Lecithin[3] | 0.20 |
| Aromas | 0.02 |

[1] commercially available,
[2] for example, pyrogenic silicon dioxide,
[3] soya lecithin.

The adhesive cream according to example 5 has good adhesion strength which lasts at least 12 hours. The adhesive cream leaves behind a fresh taste and a good, pleasantly silky sensation in the mouth.

In summary, it is established that a plant oil and/or fat is advantageously present in a quantity of from 25 to 60% by weight, from 30 to 45% by weight in relation to the total quantity of the composition, the water-soluble polymer selected from the group of cellulose derivatives is present in a quantity of from 10 to 40% by weight, from 15 to 38% by weight, or from 15 to 25% by weight in relation to the total quantity of the composition, the alkyl vinyl ether/maleic acid anhydride copolymer is present in a quantity of from 25 to 45% by weight or from 28 to 39% by weight in relation to the total quantity of the composition, the silicon dioxide is present in a quantity of from 0 to 2.5% by weight or from 0 to 1.5% by weight in relation to the total quantity of the composition, the polyethylene glycol is present in a quantity of from 0 to 15% by weight or from 0 to 10% by weight in relation to the total quantity of the composition, the trihydroxystearin is present in a quantity of from 0 to 2.5% by weight or 2.1% by weight in relation to the total quantity of the composition and the phosphoglyceride is present in a quantity of from 0 to 3% by weight or from to 2% by weight in relation to the total quantity of the composition. It was in particular established that the trihydroxystearin is present in combination with the phosphoglyceride in a quantity of from 0 to 2.5% by weight or from 0 to 1% by weight in relation to the total quantity of the composition. It was further established that the total quantity of the trihydroxystearin, silicon dioxide and phosphoglyceride contained in total should not exceed the quantity of a maximum of 10% by weight, a maximum of 5% by weight, or a maximum of 4% by weight in relation to the total quantity of the composition.

The invention claimed is:

1. A composition of an adhesive cream for tooth prostheses, comprising:
   at least one of a plant oil and a plant fat comprised of at least 20% by weight of at least one unsaturated fatty acid;
   at least one water-soluble polymer selected from the group comprising cellulose derivatives;
   at least one alkyl vinyl ether/maleic acid anhydride copolymer; and
   at least one trihydroxystearin.

2. The composition of claim 1, wherein the at least one of a plant oil and a plant fat is comprised of at least 40% by weight of at least one unsaturated fatty acid.

3. The composition of claim 1, wherein the at least one of a plant oil and a plant fat is comprised of at least 50% by weight of at least one higher fatty acid having a chain length of at least 12 C atoms.

4. The composition of claim 3, wherein the at least one higher fatty acid has a chain length of from 12 to 26 C atoms.

5. The composition of claim 1, wherein the at least one of a plant oil and a plant fat comprises more than 25% by weight of the composition.

6. The composition of claim 1, wherein the at least one of a plant oil and a plant fat comprises a maximum of 60% by weight of the composition.

7. The composition of claim 1, wherein the at least one of a plant oil and a plant fat comprises an olive oil.

8. The composition of claim 1, wherein the at least one water-soluble polymer comprises from 10 to 40% by weight of the composition.

9. The composition of claim 1, wherein the at least one alkyl vinyl ether/maleic acid anhydride copolymer comprises from 25 to 39.5% by weight of the composition.

10. The composition of claim 1, further comprising at least one substance selected from the group consisting of silicon dioxides, talcum, stearates, magnesium stearate, aluminum stearate, phosphoglycerides, and polyethylene glycols.

11. The composition of claim 10, wherein the at least one substance comprises from 0.001% to 2.5% by weight of the composition.

12. The composition of claim 10, wherein the polyethylene glycols comprise from 0.001 to 15% by weight of the composition.

13. The composition of claim 12, wherein the polyethylene glycols have a molar mass in the range from 100,000 to 7,000,000 g/mol.

14. The composition of claim 10, wherein the silicon dioxide comprises from 0.001 to 5% by weight of the composition.

15. The composition of claim 1, wherein the trihydroxystearin comprises from 0.001 to 2.5% by weight of the composition.

16. The composition of claim 10, wherein the phosphoglycerides comprise from 0.001 to 3% by weight of the composition.

17. The composition of claim 16, wherein the phosphoglycerides are selected at least from the group consisting of lecithins.

18. The composition of claim 1, further comprising at least one additive selected from the group consisting of stabilizers, antioxidants, flavorings, colorings and admixtures thereof.

19. The composition of claim 1, further comprising less than 1% by weight of a composition of zinc.

20. The composition of claim 19, wherein the zinc comprises between 0.01% and 1% by weight of the composition.

21. The composition of claim 1, comprising 25 to 60% by weight of the composition of the at least one of a plant oil and a plant fat, 10 to 40% by weight of the composition of the composition of at least one water-soluble polymer selected from the group consisting of cellulose derivatives and 25 to 45% by weight of the composition of at least one alkyl vinyl ether/maleic acid anhydride copolymer.

22. The composition of claim 1, comprising 0 to 15% by weight of a composition of polyethylene glycols, 0 to 3% by weight of the composition of phosphoglycerides, 0.001 to 2.5% by weight of the composition of the trihydroxystearin, 0 to 5% by weight of the composition of silicon dioxide and 0 to 10% by weight of the composition of at least one additive.

23. A composition of an adhesive cream for tooth prostheses, comprising:
   at least one of a plant oil and a plant fat comprised of at least 20% by weight of at least one unsaturated fatty acid;
   at least one water-soluble polymer selected from the group comprising cellulose derivatives;
   at least one alkyl vinyl ether/maleic acid anhydride copolymer; and
   at least one phosphoglyceride.

24. The composition of claim 23, wherein the at least one of a plant oil and a plant fat is comprised of at least 40% by weight of at least one unsaturated fatty acid.

25. The composition of claim 23, wherein the at least one of a plant oil and a plant fat is comprised of at least 50% by weight of at least one higher fatty acid having a chain length of at least 12 C atoms.

26. The composition of claim 25, wherein the at least one higher fatty acid has a chain length of from 12 to 26 C atoms.

27. The composition of claim 23, wherein the at least one of a plant oil and a plant fat comprises more than 25% by weight of the composition.

28. The composition of claim 23, wherein the at least one of a plant oil and a plant fat comprises a maximum of 60% by weight of the composition.

29. The composition of claim 23, wherein the at least one of a plant oil and a plant fat comprises an olive oil.

30. The composition of claim 23, wherein the at least one water-soluble polymer comprises from 10 to 40% by weight of the composition.

31. The composition of claim 23, wherein the at least one alkyl vinyl ether/maleic acid anhydride copolymer comprises from 25 to 39.5% by weight of the composition.

32. The composition of claim 23, further comprising at least one substance selected from the group consisting of silicon dioxides, talcum, stearates, magnesium stearate, aluminum stearate, polyethylene glycols and trihydroxystearin.

33. The composition of claim 32, wherein the at least one substance comprises from 0.001% to 2.5% by weight of the composition.

34. The composition of claim 32, wherein the polyethylene glycols comprise from 0.001 to 15% by weight of the composition.

35. The composition of claim 34, wherein the polyethylene glycols have a molar mass in the range from 100,000 to 7,000,000 g/mol.

36. The composition of claim 32, wherein the silicon dioxide comprises from 0.001 to 5% by weight of the composition.

37. The composition of claim 32, wherein the trihydroxystearin comprises from 0.001 to 2.5% by weight of the composition.

38. The composition of claim 23, wherein the phosphoglycerides comprise from 0.001 to 3% by weight of the composition.

39. The composition of claim 23, wherein the phosphoglycerides are selected at least from the group consisting of lecithins.

40. The composition of claim 23, further comprising at least one additive selected from the group consisting of stabilizers, antioxidants, flavorings, colorings and admixtures thereof.

41. The composition of claim 23, further comprising less than 1% by weight of a composition of zinc.

42. The composition of claim 41, wherein the zinc comprises between 0.01% and 1% by weight of the composition.

43. The composition of claim 23, comprising 25 to 60% by weight of the composition of the at least one of a plant oil and a plant fat, 10 to 40% by weight of the composition of the composition of at least one water-soluble polymer selected from the group consisting of cellulose derivatives and 25 to 45% by weight of the composition of at least one alkyl vinyl ether/maleic acid anhydride copolymer.

44. The composition of claim 23, comprising 0 to 15% by weight of the composition of polyethylene glycols, 0.001 to 3% by weight of the composition of phosphoglycerides, 0 to 2.5% by weight of the composition of the trihydroxystearin, 0 to 5% by weight of the composition of silicon dioxide and 0 to 10% by weight of the composition of at least one additive.

* * * * *